United States Patent [19]

Nirschl

[11] 4,441,490

[45] Apr. 10, 1984

[54] WRIST BRACE

[76] Inventor: Robert P. Nirschl, 4143 N. River St., Arlington, Va. 22207

[21] Appl. No.: 421,966

[22] Filed: Sep. 23, 1982

[51] Int. Cl.³ .............................................. A61F 5/10
[52] U.S. Cl. .................................... 128/77; 273/54 B
[58] Field of Search ..................... 128/77, 87 R, 89 R, 128/165, DIG. 15; 273/54 B; 2/161 A, 162

[56] References Cited

U.S. PATENT DOCUMENTS

| | | | |
|---|---|---|---|
| 2,287,821 | 6/1942 | O'Donovan | 128/77 |
| 3,327,703 | 6/1967 | Gamm | 128/77 |
| 3,779,550 | 12/1973 | Benoun et al. | 273/54 B |
| 3,815,908 | 6/1974 | Hashimoto | 273/54 B |
| 4,198,709 | 4/1980 | Clayton | 273/54 B |

Primary Examiner—John D. Yasko
Attorney, Agent, or Firm—Staas & Halsey

[57] ABSTRACT

A brace for supporting the human wrist comprising a flexible pad having a main body, a substantially triangular projection extending therefrom, and a rigid angled reinforcing member positioned parallel to the metacarpals and centrally of the projection and main body for applying pressure to the wrist and dorsal area of the hand. The brace is adapted to be tightly secured to the wrist and hand without slippage and is constructed of a two-layer laminate of cloth and foam rubber. The pad is easily tightened about the wrist by means of Velcro fastener strips attached thereon, and the projection is further secured to the hand by an elastic strap which is attached to one end of the projection, crosses the palm and reattaches by a Velcro fastener to the other side of the projection. The elastic strap also increases the pressure exerted by the projection over the dorsal area of the hand, which in turn aids in stabilizing and supporting the area applying pressure to the wrist.

12 Claims, 5 Drawing Figures

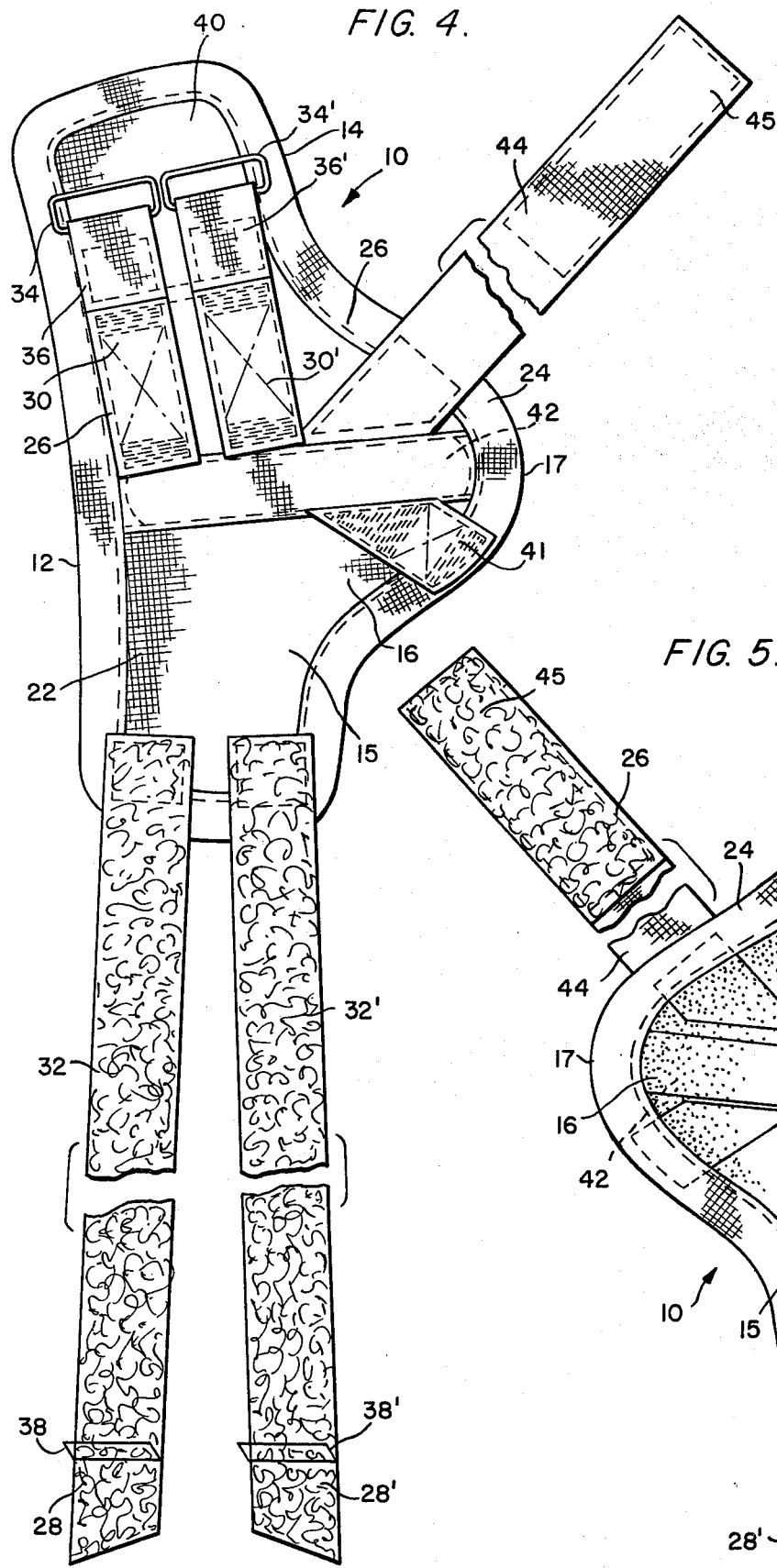
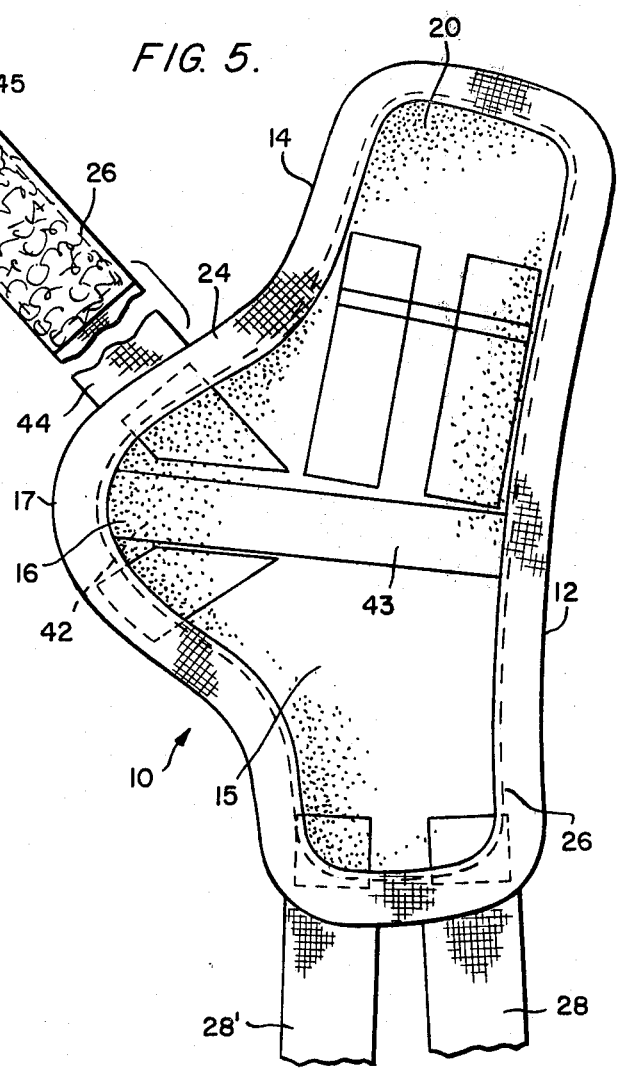

WRIST BRACE

BACKGROUND OF THE INVENTION

1. Field of the Invention

This invention pertains to a brace for supporting the wrist. In particular, this invention relates to a brace for preventing and relieving injuries and supporting the bones, muscles and tendons of the wrist by applying external pressure over the wrist and dorsal section of the hand to thereby relieve tension normally exerted on the wrist during physical activity.

2. Description of the Prior Art

Wrists are used very frequently in the course of many activities, especially, for example in strenuous sports. Such strenuous activity may sprain or may otherwise injure the wrist unless it is effectively braced. In addition, once an injury has occurred to the wrist it is necessary to support the joint to aid healing and to alleviate discomfort due to the injury.

In order to alleviate, and preferably avoid altogether, adverse affects on wrists from overwork or injury, there have become known a number of wrist braces. For example, U.S. Pat. No. 1,790,381 issued to Keller discloses a leather wrist band which surrounds the wrist and partly extends across one side of the dorsal area of the hand. In addition, three straps are used to attach the strap to the wrist and hand. However, the brace disclosed in this patent is a relatively flexible design and thus does not provide optimum support for the wrist in relation to the freely moving hand. Further, the Keller brace is difficult to secure to the hand, especially when the pad is applied by the wearer himself and when the wearer is using the hand which by nature is less dexterous.

Another wrist brace design is disclosed in U.S. Pat. No. 4,309,991, issued to DeMarco. This patent describes a wrist brace which is a relatively flat flexible, elastic sleeve for insertion therethrough of the hand so that the thumb fits through an aperture in the sleeve and a long Velcro strap extends around the hand and wrist to secure the brace. However, this flexible brace, like the Keller design, does not provide optimum support for the wrist. In addition, by its palm side extension it restricts the wearer's use of his fingers and palm, and/or may constrict blood flow, as is characteristic of elastic braces.

Thus, it can be seen that the prior art wrist brace devices for preventing or alleviating wrist injuries and discomfort still have inherent disadvantages. None of the known prior art devices has the novel features of the invention disclosed herein for eliminating these disadvantages while maintaining a low-cost, easily manufactured brace.

OBJECTS OF THE INVENTION

In light of the above-mentioned disadvantages in the prior art wrist braces, it is a primary object of the present invention to provide a wrist brace which can be tightly wrapped about the wrist and hand with a substantially uniform pressure over a sufficiently wide area of the wrist and dorsal hand to maximize the dissemination of forces placed thereon.

It is another object of the present invention to provide a wrist brace resisting slippage from the wrist during vigorous athletic motion such as that occurring during a game of tennis.

It is a further object of the present invention to provide a wrist brace which does not impair the dexterity of the wearer, especially the use of his fingers and palm.

It is another object of the present invention to provide a wrist brace which firmly supports the statistically key pathological areas of common wrist injury, namely:
(1) radial carpal and radial-ulnar joints; and
(2) wrist ligaments and tendons (especially the ulnar collateral ligment and the triangular cartilage).

It is still another object of the present invention to provide a wrist brace using a strong pad of rugged, long wearing characteristics, which maintains its appearance and utility over a prolonged use.

It is another object of the present invention to provide a wrist brace which is adjustable, flexible and non-cumbersome, thus ensuring convenient and comfortable wear during daily activities.

Finally, it is an object of this invention to provide a wrist brace which can be secured to the wrist and hand and properly adjusted without assistance from a second person.

SUMMARY OF THE INVENTION

These and other objects of the invention are achieved by a wrist brace comprising a flexible elongated pad having a main body and a substantially triangular projection extending therefrom, which together contour and support the upper hand and wrist. The main body has a length greater than its width, one long edge slightly arcuately-shaped and of a predetermined length measured longitudinally of said elongated pad, and has an opposed long edge with a portion thereof non-parallel to and extending away from said arcuately-shaped long edge and of a predetermined length measured longitudinally of said elongated pad. One end of the main body has two Velcro fastener strips attached to the outer surface of the outer layer and the other end of the main body has two rings attached to the outer surface of the other side whereby the pad can be fastened around the wrist. The substantially triangular projection extends from the opposed long edge of the main body for positioning over the dorsal area of the hand. An angled metal reinforcing member is partially positioned within the main body parallel to the forearm and extends into the substantially triangular projection to contour the dorsal side of the hand, and an adjustable elastic strap is placed between the thumb and index finger, spans across the palm and is reattached by a Velcro closure to the projection near the small finger side of the brace. The purpose of the adjustable elastic strap is to aid in stabilizing the brace and to add extra support.

The wrist brace of the invention is configured to facilitate the exertion of an even counterforce pressure over a broad area of the wrist and dorsal hand during relative movement thereof, without significantly impairing the dexterity of the hand and wrist of the wearer. Thus, the objects of this invention are satisfied by providing an accurately fitting wrist brace which maximally disseminates forces broadly over the wrist area.

BRIEF DESCRIPTION OF THE DRAWINGS

These and other objects and advantages of the invention, which will become apparent to those skilled in the art, are referenced to the following drawings in which:

FIG. 4 is a top plan view of the wrist brace of the present invention; and

FIG. 5 is a bottom plan view of the wrist brace of the present invention.

DETAILED DESCRIPTION OF THE PREFERRED EMBODIMENTS

Figure 1:
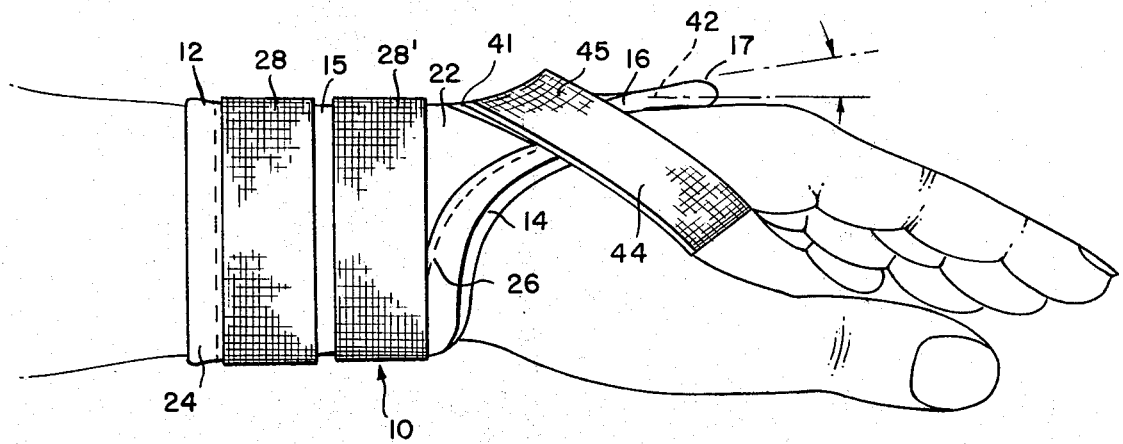
FIG. 1 is a left side view of the wrist brace of the present invention secured to the wrist and hand, illustrating particularly the placement of the fastening means and the positioning of the projection over the dorsal area of the hand.

As best seen in FIGS. 4 and 5, the wrist brace of the preferred embodiment of the present invention comprises an elongated pad 10 having one slightly convexly, arcuately-shaped long edge 12 and having an opposing long edge 14 with a portion thereof non-parallel to edge 12. The pad 10 has two main portions: a main body portion 15 defined substantially by the edges 12 and 14, and a substantially triangular projection 16 extending away from the convexly arcuately-shaped long edge 12.

This configuration provides for support of the wrist by the exertion of an even pressure around the wrist and hand, and particular pressure on the dorsal side of the hand, while still leaving the fingers and palm relatively free, as will be described hereafter. Thus, the pad extends over a wide area but does not significantly impair use of the hand.

Figure 3:
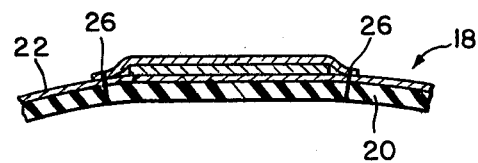
FIG. 3 is a cross-sectional view of the wrist brace shown in FIG. 2, taken along line 3—3, illustrating particularly the location of the reinforcing member.

As best seen in FIG. 3, pad 10 comprises a laminate 18 with one of the layers being a polymeric foam bottom layer 20, which is preferably foam rubber of about one-eighth inch to one-fourth inch thickness. Extra padding is used at the central portion of the pad 10 at the projection 16.

A suitable laminate of foam rubber and cotton is commercially available from PROTEK-TOE PRODUCTS, of Union, New Jersey. It is possible to use other foams than foam rubber, but the foam should be selected so that it is highly resilient, has similar "fight back" properties so it tends to resist compression, and has a coefficient of friction sufficiently similar to that of foam rubber, whereby it resists slipping even when the skin underneath the brace begins to sweat. Preferably the surface of the foam rubber is smooth appearing and the pore size of the foam at the surface is very tiny, giving the outer surface of the foam a skin-like appearance.

The laminate 18 is also comprised of a top layer 22, which is a relatively inelastic sheet, preferably cotton duck cloth. The top layer 22 is relatively inelastic because inelastic material minimizes circulatory blockage, such as is present with the use of elastic wrappings and supports known in the prior art.

When the pad 10 is wrapped about the wrist and hand, the bottom layer 20 and the top layer 22 are the inner and outer layers, respectively, of the wrist brace.

The laminate 18 is preferably bordered by a binding strip 24, which is an elasticized fabric. The elastic binding strip 24 is sewn on, as are all other attachments to the pad 10, by stitching 26 which is sewn through the foam rubber side. By sewing through the foam rubber side is meant stitching with the foam rubber side in the upper position, the stitches 26 causing the bottom foam rubber layer 20 to compress. The stitches, therefore, are indented below the surface that is in contact with the skin, thereby lessening the danger of skin irritation due to abrasion caused by raised stitching.

As best seen in FIG. 4, to one end of the pad 10 is attached a pair of flexible Velcro or equivalent fastener strips 28 and 28' for attaching the main body portion 15 to the wrist of the wearer. Each fastener strip has hooked portions 30 and 30' and looped portions 32 and 32'. The other end of the pad has several rigid metal rings 34 and 34' attached to the flexible outer layer 22 by looped cloth ribbons 36 and 36'. The brace is kept firmly about the wrist by threading the free ends of the Velcro fastener strips 28 and 28' through the underside of rigid metal rings 34 and 34' and reversedly back for attachment to the hook ends 30 and 30' of the Velcro fastener strips 28 and 28'.

Conveniently, the free ends of the Velcro fastener strips can be looped back upon themselves and stitched, thereby forming raised portions or catches 38 and 38' which are adapted to engage the metal rings 34 and 34'. These raised portions 38 and 38' thus permit the user to form a circular, loosely engaged support through which he can insert his hand prior to final positioning of the support device about the wrist and dorsal area of the hand and tightening of the Velcro fastener strips 28 and 28'.

To facilitate tightening and to prevent misalignment of the ends of the pad 10 when the fastener strips 28 and 28' are tightly drawn, a particularly preferred embodiment shown in FIG. 3 has a plastic sheet material 40 such as celluloid or its equivalent stitched onto the upper surface of the upper layer 22 below the metal rings 34 and 34'.

Figure 2:
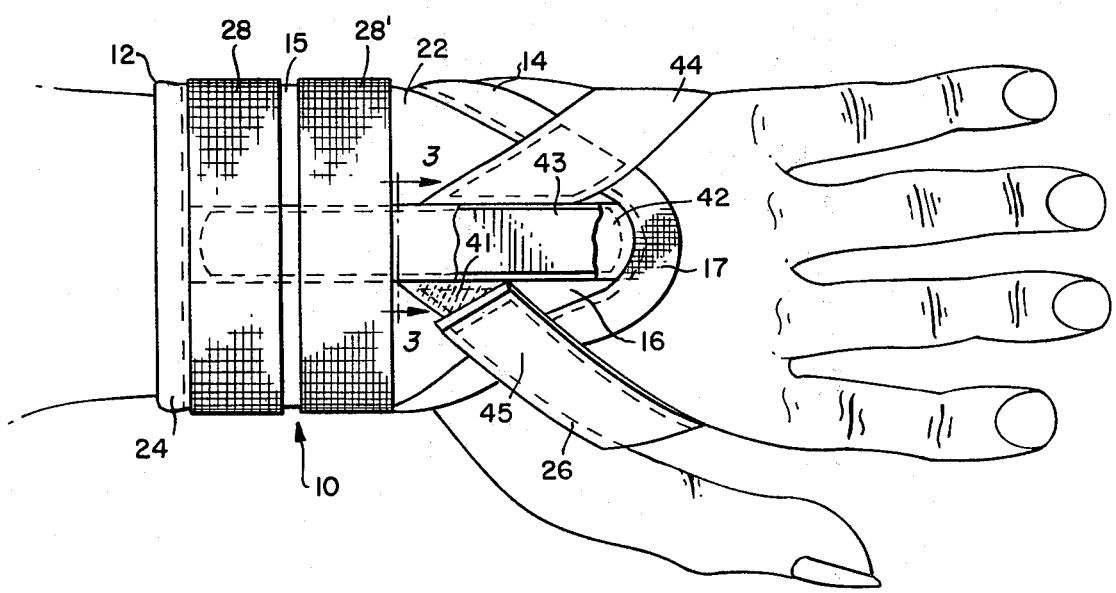
FIG. 2 is a top view of the wrist brace of the present invention secured to the wrist and hand, illustrating particularly a cut-away view of the position of the reinforcing member over the dorsal side of the hand.

As shown more clearly in FIGS. 1 and 2, the projection 16 of the wrist brace extends from edge 14 and is designed to accommodate the dorsal area of the hand in the preferred embodiment. The projection 16 is widest at the area it meets the main body 15 and tapers to form a rounded end 17 over the metacarpals. The projection 16 has on its top layer 22 a looped-cloth area 41 for joining with the Velcro-hooked end of an elastic strap 44 which will be described hereafter. This configuration ensures that the brace is capable of covering much of the dorsal side of the hand for adequate stabilization and support of the wrist.

As best seen in FIGS. 1, 2 and 4, reinforcing member 42, which is, e.g., a rigid strip of metal or a synthetic resin, provides additional stabilizing strength and support for the wrist brace. The reinforcing member 42 is positioned parallel to the forearm partially within the main body 15 of the pad 10 and partially extends into the projection 16. The reinforcing member 42 is enclosed by an inelastic rectangular cloth strip 43 sewn to the outer layer 22 of the pad 10.

Member 42 is also angled to contour the dorsal area of the hand. The reinforcing member 42 can be bent by the user as preferred to exert different amounts of pressure upon the dorsal area of the hand. Preferably, the reinforcing member 42 is bent at the end farthest away from edge 12 to an angle of about 10 degrees away from the hand.

An elastic strap 44 is also provided stitched to one side of the projection 16. The strap 44 has a free end 45 covered on one side by Velcro hooked material for fastening to the Velcro looped area 41 on the top layer of the projection 16. The elastic strap 44 extends across the palm, and its free and 45 is reattached as stated, to the Velcro looped area 41 of the projection 16.

This fastening configuration provides adequate adjustment by the wearer of the strap 44 on the projection 16. The elastic strap 44 is intended to firmly hold the projection down against the dorsal area of the hand.

To summarize application of the wrist brace, the wearer places the catches 38 and 38' on strips 28 and 28' through the respective rings 34 and 34' to hold the brace in a sutstantially closed circle configuration. The wearer then inserts his hand through the brace until the projection 16 rests on the dorsal area of the hand. The free ends of Velcro fastening strips 28 and 28' are pulled further through rings 34 and 34', looped back upon themselves, and fastened to the respective Velcro hooked portions 30 and 30'. In addition, elastic strap 44 is pulled across the palm and reattached to the projection 16 at the Velcro hooked area 41.

It has been found that convenient dimensions for this wrist brace are in the range of 4 to 6 inches between the end 17 of the projection 16 and the convexly arcuately-shaped long edge 12, and 7 to 9 inches measured linearly longitudinally along the main body 15 of the pad 10. Size of the support device is not important but it is advantageous to have several sizes, each sufficient to be wrapped about the wrist and hand without extensive overlap.

When the brace of this embodiment is firmly fastened about the wrist and hand, as shown in FIGS. 1 and 2, it provides pressure about the wrist, and especially against the dorsal side of the hand, and thus disseminates any excessive concentration of forces at and about the wrist during athletic exertion. This brace is configured to avoid immobilizing the hand of the wearer and thus avoids hinderance of the wearer's athletic activities while still providing musculo-tendinous support over a broad area.

The brace of the invention can be used for the prevention of other injuries and alleviation of the pain associated with these injuries, e.g., by those who work at occupations such as carpentry which because of their nature prove to cause injuries similar to those caused by sports.

While the preferred embodiment of the brace of this invention, especially suited for the disclosed specialized applications, has been disclosed with particularity above, numerous modifications of the same within the scope of the invention will be readily apparent to those skilled in the art. Additionally, various configurational modifications of the brace of this device to facilitate application of the invention to the wrist and hand, will occur to those skilled in the art and are considered also to be encompassed by this invention. Thus, the scope of the invention of this wrist brace is to be limited solely by the claims appended hereto.

I claim:

1. A brace capable of being wrapped about the wrist and dorsal area of the hand and capable of applying pressure to a wide area of the wrist and hand to thereby relieve internal tension of the wrist, comprising: an elongated pad, said paid being substantially flexible in all directions and having a laminate with an inner layer of resilient foamed material bonded to an outer layer of substantially inelastic flexible sheet; having,
    (a) a main body with one long edge slightly convexly arcuately-shaped, an opposing long edge, a first end and a second end;
    (b) a substantially triangular projection extending away from the main body having a rigid reinforcing member attached parallel to the forearm along the main body and the projection; and
    (c) fastening means for securing the brace tightly about the wrist and dorsal area of the hand.

2. The brace according to claim 1, wherein the fastening means comprise at least one fastener strip attached to the outer surface of the outer layer at the first end of the elongated pad for attachment to the second end of the pad.

3. The brace according to claim 1, wherein the fastening means comprise an elastic strap which extends from one side of the substantially trangular projection around the palm of the hand, and reattaches to the other side of the projection.

4. The brace of claim 1, wherein said fastening means comprises:
    (a) a plurality of Velcro looped material fastener strips, each strip having a first end attached to the outer surface of the outer layer at the first end of the elongated pad, and each strip having a second end a free and, a corresponding plurality of rings and a corresponding plurality of hooked Velcro material strips attached to the outer surface of the outer layer at the second end of the pad, wherein each of the plurality of Velcro looped material fastener strips partially overlaps the pad, and whereby the pad can be fastened around the wrist by threading each said free end of the Velcro looped strips through the corresponding rings and reversedly drawing the free end for attachment to the Velcro-hooked material strips, and
    (b) an elastic strap, which is attached to one side of the substantially triangular projection and has a free end covered with Velcro looped material, extends around the palm, and reattaches at the other side of the projection to Velcro hooked material.

5. The brace of claim 1, 2, 3 or 4, wherein the reinforcing member comprises a relatively stiff elongated strip of a substantially rigid synthetic resin.

6. The brace of claim 5, wherein the reinforcing member has one end bent at an angle.

7. The brace of claim 1, 2, 3 or 4, wherein the reinforcing member comprises a metal elongated strip.

8. The brace of claim 7, wherein the reinforcing member has one end bent at an angle.

9. The brace of claim 6, wherein the reinforcing member is angled at approximately 10 degrees away from the dorsal area of the hand.

10. The brace of claim 1, wherein the resilient foamed material is foam rubber.

11. The brace of claim 1, wherein the substantially inelastic flexible sheet is a woven fabric.

12. The brace of claim 8, wherein the reinforcing member is angled at approximately 10 degrees away from the dorsal area of the hand.

* * * * *

UNITED STATES PATENT AND TRADEMARK OFFICE
CERTIFICATE OF CORRECTION

PATENT NO. : 4,441,490
DATED : April 10, 1984
INVENTOR(S) : Robert P. Nirschl

It is certified that error appears in the above-identified patent and that said Letters Patent is hereby corrected as shown below:

Column 5, line 1, "and" should be --end--.
         line 10, "sutstantially" should be --substantially--.
         line 56, after "is" insert --not--.
Column 6, line 19, "trangular" should be --triangular--.
         line 28, "end" should be --end,--; "and," should be --end,--.

Signed and Sealed this

Fourth Day of September 1984

[SEAL]

Attest:

GERALD J. MOSSINGHOFF

Attesting Officer

Commissioner of Patents and Trademarks